(12) United States Patent
Broda et al.

(10) Patent No.: US 6,365,752 B1
(45) Date of Patent: Apr. 2, 2002

(54) PROCESS FOR PREPARING 1-SUBSTITUTED 5-HYDROXY-IMIDAZOLINE-2,4-DIONES AND 1-SUBSTITUTED 5-ALKOXY-IMIDAZOLINE-2,4-DIONES

(75) Inventors: Witold Broda, Neunkirchen-Seelscheid (DE); Luc Jerome Vanmaele, Lochristi (BE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/618,239

(22) Filed: Jul. 18, 2000

(30) Foreign Application Priority Data

Jul. 21, 1999 (DE) .......................................... 199 34 231

(51) Int. Cl.[7] .......................................... C07D 233/02
(52) U.S. Cl. .................................................. 548/317.5
(58) Field of Search ...................................... 548/317.5

(56) References Cited

U.S. PATENT DOCUMENTS 4,647,574 A * 3/1987 Ienaga et al. ................ 514/390

FOREIGN PATENT DOCUMENTS

| EP | 160618 | 11/1985 |
| JP | 62145068 | 6/1987 |
| JP | 6-100543 | 4/1994 |
| JP | 9-227526 | 9/1997 |

OTHER PUBLICATIONS

Advanced Organic Chem., (month unavailable) 1985, 3rd edition, chapter 8, pp. 218–236, J. March, "Acids and Bases".

Tetrahedron Letters, vol. 23, No. 27 (month unavailable), 1982, pp. 2741–2744, L. E. Overman et al, The Cyanomethyl Group For Nitrogen Protection And Iminium Ion Generation In Ring–Enlarging Pyrrolidine Annulations. A Short Synthesis Of The Amaryllidaceae Alkaloid d, 1–CRININE[1].

Huaxne Skiji (month unavailable), 1993, 15(1), pp. 15–16, Yu Ding et al, "Synthesis of 1–Benzle–5–Ethoxy–2, 4–Imidazolidinedione".

Tetrahedron, Bd. 33, (month unavailable), 1977, Seiten 1191–1196, XP000940734, Dov Ben–Ishai, et al, "The Reactions Of Ureas With Glyoxylic Acid And Methyl Glyoxylate".

* cited by examiner

Primary Examiner—T. A. Solola
Assistant Examiner—Sonya Wright
(74) Attorney, Agent, or Firm—Joseph C. Gil; Richard E. L. Henderson; Diderico van Eyl

(57) ABSTRACT

A process for preparing specific 1-substituted 5-hydroxy-imidazoline-2,4-diones by reacting glyoxylic acid with N-substituted ureas is provided, where this process is carried out in a 10–80% strength aqueous solution and in the presence of an acid catalyst. The 1-substituted 5-hydroxy-imidazoline-2,4-diones can subsequently be converted in a further reaction step to give 1-substituted 5-alkoxy-imidazoline-2,4-diones.

17 Claims, No Drawings

PROCESS FOR PREPARING 1-SUBSTITUTED 5-HYDROXY-IMIDAZOLINE-2,4-DIONES AND 1-SUBSTITUTED 5-ALKOXY-IMIDAZOLINE-2,4-DIONES

FIELD OF THE INVENTION

The invention relates to a novel process for preparing specific 1-substituted 5-hydroxy-imidazoline-2,4-diones starting from N-substituted urea and glyoxylic acid and the further conversion of these 1-substituted 5-hydroxy-imidazoline-2,4-diones into 1-substituted 5-alkoxy-imidazoline-2,4-diones.

BACKGROUND OF THE INVENTION

1-Benzyl-5-ethoxy-imidazoline-2,4-dione of the formula (A)

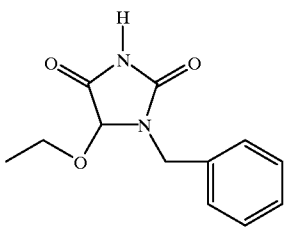

(A)

(hereinafter referred to as "BEH") belongs to the class of hydantoins and is also referred to as 1-benzyl-5-ethoxyhydantoin. BEH, its derivatives which are substituted on the benzyl ring and also other 1-substituted 5-alkoxy-imidazoline-2,4-diones have gained increasing importance as intermediates in the preparation of medicaments, insecticides, textile assistants and amino acids. BEH itself is required, in particular, for the preparation of photochemicals.

It is known from Huaxue Shiji 1993, 15(1), 15–16, that BEH can be prepared from the corresponding 1-benzylhydantoin by bromination or chlorination in the 5 position to give the corresponding 1-benzyl-5-halogenohydantoins and further reaction of these halogenohydantoins with ethanol (see reaction equation below).

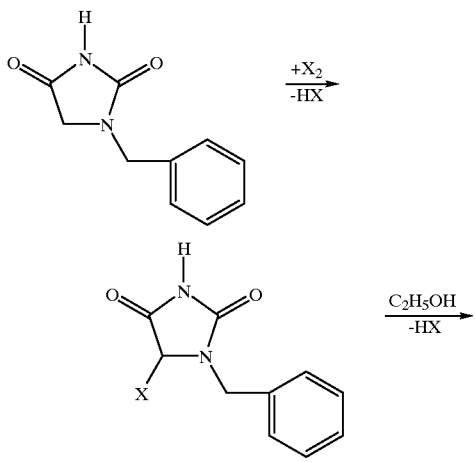

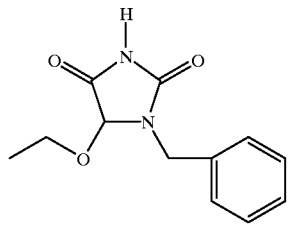

$X_2 = Cl_2, Br_2$

The above reaction sequence has a number of disadvantages: thus, the use of free bromine or chlorine is difficult in terms of industrial handling and is not without danger. Furthermore, large amounts of hydrogen halides are obtained in the halogenation itself and also in the subsequent halogen replacement, and these have to be disposed of.

The starting material for the abovementioned chlorination or bromination, namely 1-benzylhydantoin, also referred to as 1-benzyl-imidazoline-2,4-dione, in turn has to be prepared via a number of steps:

a) by reaction of N-benzylaminoacetonitrile (a product of the addition of benzylamine and hydrocyanic acid onto formaldehyde) and cyanic acid (JP 06 100 543 A2) or b) by reaction of N-benzylglycine (or its derivatives) and urea or cyanic acid (Huaxue Shiji 1993 15(1), 15–16).

The starting material for the abovementioned synthetic route a), viz. N-benzyl-aminoacetonitrile, is prepared by reaction of benzylamine and formaldehyde with the extremely toxic hydrocyanic acid (see also Tetrahedron Letters [23], 27 (1982), 2741–4). The starting material for the synthetic route b), viz. N-benzylglycine, also firstly has to be prepared by reaction of glycine with benzyl chloride or of chloroacetic acid with benzylamine. The reaction of N-benzylaminoacetonitrile or N-benzylglycine as per a) or b) is carried out either by fusion with urea for a long time or by reaction with the toxic cyanic acid. Both methods give 1-benzyl-hydantoin in only low yields: thus, according to Huaxue Shiji 1993, 15(1) 15–16, the reaction of N-benzylglycine (obtained by reaction of benzylamine with chloroacetic acid) with cyanic acid gives 1-benzylhydantoin in a yield of only 39.5% and the reaction of N-benzylglycine with urea gives 1-benzylhydantoin in a yield of only 45.6%. The subsequent bromination of the 1-benzylhydantoin and treatment with ethanol again proceeds in only a low yield of 42.7%.

Furthermore, Huaxue Shiji 1993 15(1), 15–16 merely states that glyoxylic acid can in principle be used as starting material for a reaction with a substituted urea. However, no information is given regarding the reaction conditions which have to be adhered to to carry out such a reaction successfully.

In addition, it is known from JP 09 227 526 A2 that N-substituted ureas of the formula RN"HCONH$_2$, where R"=alkyl or aryl, can be reacted with alkyl glyoxylate alkyl hemiacetals of the formula ROCH(OH)COOR', where R, R'=alkyl, in a solvent or a solvent mixture. This firstly forms, apart from a large number of other compounds, the corresponding 1-alkyl- or 1-aryl-substituted 5-hydroxy-hydantoin of the formula (B).

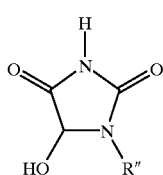
(B)

In the case of R"=benzyl, the reaction thus forms 1-benzyl-5-hydroxyhydantoin of the formula (C)

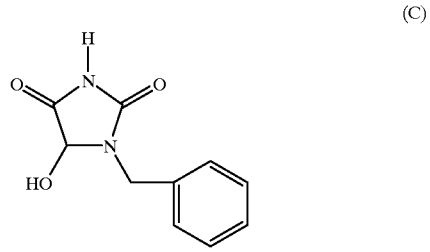
(C)

in addition to many other compounds. The multicomponent reaction mixture, which contains, inter alia, the 1-alkyl- or 1-aryl-substituted 5-hydroxy-hydantoin, is obtained as a viscous, oily mass and is virtually impossible to purify. Before the further reaction, it has to be carefully dewatered and subsequently reacted with an alcohol and mineral acid by prolonged heating, which again forms, owing to the impure composition of the reaction mixture used, a mixture of a number of compounds, including the desired 1-alkyl- or 1-aryl-5-alkoxy-imidazoline-2,4-dione.

The isolation of the desired 1-alkyl- or 1-aryl-5-alkoxy-imidazoline-2,4-dione is therefore complicated and has to be carried out by column chromatography. This separation has been described only on the gram scale, is hardly feasible in industry and gives the desired product in a yield of only 44% and in unknown purity (JP 09 227 526 A2, Example 1).

In addition, the starting compounds for this synthesis, i.e. the alkyl glyoxylate alkyl hemiacetals, firstly have to be synthesized by independent routes. They are obtained as mixtures of hemiacetals and acetals and likewise have to be purified in a costly manner.

EP-A-0 160 618 describes the reaction of glyoxylic esters or o-alkylglyoxylic esters (glyoxylic ester alkoxides) with N-alkylureas, N-cycloalkylureas, N,N'-dialkylureas or N,N'-dicycloalkylureas in a solvent such as water and/or acetic acid. In addition, it is established that this reaction can also be carried out using glyoxylic acid itself. In Example 2 of EP-A-0 160 618, the reaction of glyoxylic acid with N-methylurea is carried out in an aqueous acetic acid solution. The product obtained is said to be 5-hydroxy-3-methylhydantoin, but no information is given on the yield or selectivity of the reaction. Repeating the in-principle reaction of glyoxylic acid with N-methylurea gave only small amounts of a greasy crystalline product which represents a very complicated mixture of many substances and whose separation by crystallization is not practical. NMR analysis of this crystalline product indicated, alongside many other compounds in small amounts, the two isomeric 1- and 3-methyl-5-hydroxyhydantoins in approximately equal amounts of about 10%. In view of the lack of a yield figure in Example 2 of EP-A-0 160 618, it therefore has to be assumed that only small amounts of 1-methyl-5-hydroxy-hydantoin were isolated there. The process of EP-A-0 160 618 using alkyl- or cycloalkyl-substituted ureas can therefore not be regarded as a suitable possible method of preparing 1-alkyl-5-hydroxy-hydantoins.

Tetrahedron 33 (1977), pp. 1191–1196, discloses the reaction of glyoxylic acid with N-methylurea. However, without use of a catalyst, this reaction in methanol gives 5-methoxy-3-methylhydantoin.

Since the demand for 1-substituted 5-alkoxy-imidazoline-2,4-diones is continually increasing in view of the many possible applications mentioned above, it is an object of the present invention to provide a process by means of which the 1-substituted 5-hydroxy-imidazoline-2,4-diones required as intermediates for the synthesis of the 1-substituted 5-alkoxy-imidazoline-2,4-diones can be prepared in high yield and high purity using simple-to-handle and nontoxic chemicals. In particular, the process to be provided should make complicated purification of the 1-substituted 5-hydroxy-imidazoline-2,4-diones, e.g. by column chromatography, superfluous.

SUMMARY OF THE INVENTION

These and other features, aspects, and advantages of the present invention will become better understood with reference to the following description and appended claim.

This object is achieved by a process for preparing 1-substituted 5-hydroxy-imidazoline-2,4-diones of the formula (I)

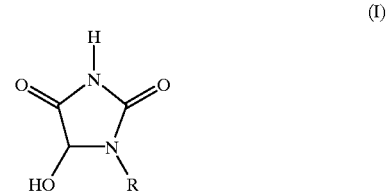
(I)

where R represents a substituted or unsubstituted $C_6$–$C_{12}$-aryl radical or a substituted or unsubstituted $C_7$–$C_{18}$-aralkyl radical, by reacting glyoxylic acid with an N-substituted urea of the formula RNH—CO—NH$_2$, where R is as defined above, characterized in that the process is carried out in a 10–80% strength aqueous solution in the presence of an acid catalyst.

DESCRIPTION OF THE INVENTION

Surprisingly, the reaction of glyoxylic acid and the N-substituted urea in aqueous solution and in the presence of the acid catalyst can be carried out successfully and in a controlled manner. It is essential that the reaction is carried out in aqueous solution. This results in the glyoxylic acid being predominantly present in the form of the hydrate.

The process of the invention displays a high selectivity to the 1-substituted 5-hydroxy-imidazoline-2,4-dione, which is at least 60%, mostly at least 70% and often even 75% or more. Apart from the 1-substituted 5-hydroxy-imidazoline-2,4-dione, the by-products which are possible according to the following reaction equation are formed in only very small amounts.

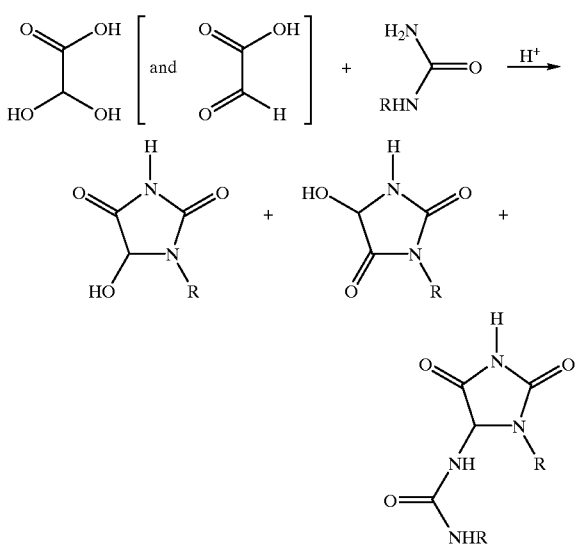

The N-substituted ureas used in the process of the invention have the formula RNH—CO—NH$_2$, where R represents a substituted or unsubstituted C$_6$–C$_{12}$-aryl radical or a substituted or unsubstituted C$_7$–C$_{18}$-aralkyl radical. The aryl radicals may be substituted by 1, 2, 3, 4 or 5 identical or different radicals selected from the group consisting of halogen, preferably chlorine, C$_1$–C$_{12}$-alkyl, preferably methyl, NO$_2$, C$_1$–C$_{12}$-alkoxy, preferably methoxy, and phenoxy.

Preference is given to using N-substituted ureas of the formula RNH—CO—NH$_2$, where R represents a substituted or unsubstituted C$_6$–C$_{10}$-aryl radical or a substituted or unsubstituted C$_7$–C12-aralkyl radical. R particularly preferably represents a benzyl radical or a benzyl radical substituted by 1, 2, 3, 4 or 5 of the abovementioned radicals, for example 3,4-dimethoxybenzyl, 4-methylbenzyl or 4-chlorobenzyl. Further suitable aralkyl radicals are 3-phenylpropyl, 1-phenylethyl and 2-phenylethyl. A suitable substituted aryl radical is 4-chlorophenyl.

The process of the invention is carried out in the presence of an acid catalyst. Acetic acid has been found to be particularly useful as catalyst. It is also possible to use catalysts whose pKa values are similar to that of acetic acid. These include potassium or sodium dihydrogenphosphates or potassium or sodium hydrogenphosphates. It is likewise possible to use other acid catalysts such as, for example, formic acid, propionic acid, boric acid, phosphoric acid, oxalic acid or alkali metal hydrogensulphates.

The molar ratio of glyoxylic acid to the N-substituted urea is (0.5–2):1, preferably (0.8–1.2):1. Particular preference is given to using equimolar or virtually equimolar) amounts of glyoxylic acid and N-substituted urea. In one embodiment, the molar ratio of glyoxylic acid to the N-substituted urea is (0.5–5):1, and preferably (0.8–2):1.

It is an essential aspect of the process of the invention that it is carried out in a 10–80% strength, preferably 20–70% strength and in particular 40–60% strength, aqueous solution. The glyoxylic acid can accordingly be used, for example, in the form of its approximately 50% strength aqueous solution.

In addition, other organic solvents such as hydrocarbons, alcohols or esters may also be present in the process of the invention.

The process of the invention is usually carried out at a temperature in the range 80–120°, preferably 95–105° C. At reaction temperatures close to the boiling point of the reaction mixture (about 100° C.), the reaction between glyoxylic acid and the N-substituted urea is rapid and complete. To achieve residual contents of N-substituted urea of less than 1%, it has been found to be useful to stir the reaction mixture for 1–2 hours after the actual reaction.

The process of the invention has been found to be particularly useful for preparing 1-benzyl-5-hydroxy-imidazoline-2,4-dione by reacting benzylurea with glyoxylic acid in aqueous solution in the presence of an acid catalyst, in particular acetic acid. The isolation of the desired product, namely the 1-substituted 5-hydroxy-imidazoline-2,4-dione of the formula (I), is usually achieved by crystallization which can be carried out either with or without additional addition of solvent. An additional solvent is preferably added to the crystallization mixture, since the crystallization then forms a crystalline product of higher purity which can be filtered off very readily. Suitable solvents are, in general, aliphatic hydrocarbons such as hexane, heptane or isooctane, halogenated hydrocarbons such as methylene chloride, substituted or unsubstituted aromatic hydrocarbons such as benzene, toluene, ethylbenzene and chlorinated benzenes or toluenes, ketones such as acetone or methyl ethyl ketone or ethers such as methyl tert-butyl ether or methyl isopropyl ether. The addition of methylene chloride or chlorobenzene has been found to be particularly useful. The crystallization temperature is preferably below 40° C. If no additional solvents are used in the crystallization, the product firstly crystallizes together with a relatively small amount of impurities. In this case in particular, it has been found useful to purify the desired product, viz. the 1-substituted 5-hydroxy-imidazoline-2,4-dione, in a simple manner by recrystallization. If the 5-benzylurea-1-benzyl-imidazoline-2,4-dione content is too high, crystallization from hot water has been found to be very advantageous. The solubility of this by-product in hot water is low, so that it can be filtered off from the hot solution of the desired 1-substituted 5-hydroxy-imidazoline-2,4-dione.

Further drying of the 1-substituted 5-hydroxy-imidazoline-2,4-dione before it is reacted further is not absolutely necessary. However, it has been found that the chemical losses in the further reaction to the 1-substituted 5-alkoxy-imidazoline-2,4-dione can be minimized if the 1-substituted 5-hydroxy-imidazoline-2,4-dione contains as little water as possible. It can therefore be dried, if desired, by simple air or vacuum drying at room temperature or elevated temperature or else by azeotropic distillation of water with the aid of suitable entrainers.

The reaction product of the reaction between glyoxylic acid and the N-substituted urea, in particular the preferred 1-benzyl-5-hydroxy-imidazoline-2,4-dione, does not, however, necessarily have to be isolated as an intermediate. It is also possible to remove the major part of the solvent from the crude reaction mixture by distillation and to react the oily product further in this form without additional treatment. It is also possible to separate the crude product as an oily lower phase by cooling the crude reaction mixture.

In a further embodiment of the process of the invention, the 1-substituted 5-hydroxy-imidazoline-2,4-diones of the formula I which have been prepared are reacted in a further step to form 1-substituted 5-alkoxy-imidazoline-2,4-diones of the formula II

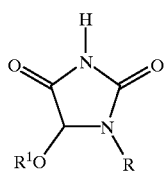

where R is as defined for the formula I and $R^1$ represents a straight-chain or branched $C_1$–$C_{18}$-alkyl radical, preferably methyl, ethyl, propyl, iso-propyl, butyl, iso-butyl, octyl or 2-ethylhexyl and in particular ethyl.

The conversion of the 1-substituted 5-hydroxy-imidazoline-2,4-diones of the formula I into the 1-substituted 5-alkoxy-imidazoline-2,4-diones of the formula II can be carried out in various ways. Suitable methods are, for example:

1) reaction of the 1-substituted 5-hydroxy-imidazoline-2,4-dione of the formula I with an alcohol of the formula $R_1OH$ in the presence of an acid catalyst.

Such an acid-catalyzed etherification is described, for example, in JP 09 227 526 A2. The alcohol used is preferably ethanol. The 1-substituted 5-hydroxy-imidazoline-2,4-dione, which has preferably been dried to form a solid and is, in particular, virtually water-free, is reacted with the alcohol. It has been found to be useful to use at least 1 mol of alcohol per mole of 1-substituted 5-hydroxy-imidazoline-2,4-dione. The acid catalyst used is preferably a protic acid. This protic acid has, in particular, a negative pKa. Such protic acids are described in "Advanced Organic Chemistry" (editor: J. March, John Wiley & Sons 1985, 3$^{rd}$ edition, chapter 8). Examples are hydrochloric acid ($pK_a=-7$), hydrobromic acid ($pK_a=-9$), sulphuric acid ($pK_a=-9$) and organic sulphonic acids ($pK_a=-6.5$). Preferred examples of organic sulphonic acids include methanesulphonic acid, trifluoromethanesulphonic acid, benzenesulphonic acid and p-toluenesulphonic acid. The acid is used in an amount of 0.001–10 mol, preferably 0.01–1 mol and in particular 0.01–0.03 mol, per mole of 1-substituted 5-hydroxy-imidazoline-2,4-dione. The reaction temperature is 0–120° C., preferably 20–100° C. The reaction time is usually 4–20 hours.

2) Reaction of the 1-substituted 5-hydroxy-imidazoline-2,4-dione of the formula I with a tri-$C_1$–$C_{18}$-alkyl orthoformate, in particular triethyl orthoformate.

This reaction is likewise acid-catalysed and proceeds very quickly. The reaction temperature is in the range 20–160° C., preferably 50–130° C. and particularly preferably 70–120° C. The reaction time is usually 1–10 hours. As catalysts, it is possible to use all acids which have been mentioned above for variant 1). The molar ratio of the trialkyl orthoformate to the 1-substituted 5-hydroxy-imidazoline-2,4-dione is usually (0.5–5):1. Particular preference is given to using equimolar amounts of trialkyl orthoformate and 1-substituted 5-hydroxy-imidazoline-2,4-dione.

3) Reaction of the 1-substituted 5-hydroxy-imidazoline-2,4-dione of the formula I firstly with thionyl chloride and subsequently with an alcohol $R^1OH$, where $R^1$ is as defined above.

The reaction temperature is in the range 50–150° C., preferably 60–100° C. The reaction time is 1–20 hours. The molar ratio of thionyl chloride to the 1-substituted 5-hydroxy-imidazoline-2,4-dione is (0.5–5):1. This reaction can be carried out in the presence or absence of an organic solvent. Suitable solvents are aliphatic, chlorinated or aromatic hydrocarbons, preferably benzene or toluene.

The 1-substituted 5-alkoxy-imidazoline-2,4-dione is preferably isolated by crystallization from its alcoholic solutions, since this is the operation which is easiest to carry out in industry.

It is also possible to prepare the product as a melt and to allow this to crystallize by cooling or to carry out the solvent crystallization from other solvents instead of ethanol.

Further complicated purification steps are not necessary, since the 1-substituted 5-alkoxy-imidazoline-2,4-dione obtained by all three routes 1), 2) and 3) has a significantly higher purity than comparable 1-substituted 5-alkoxy-imidazoline-2,4-diones prepared by the reaction sequences of the prior art. This is a result of the excellent selectivity of the process of the invention to the intermediate, namely the 1-substituted 5-hydroxy-imidazoline-2,4-dione.

The invention is further described in the following illustrative examples in which all parts and percentages are by weight unless otherwise indicated.

EXAMPLE 1

Preparation of 1-benzyl-5-hydroxy-imidazoline-2,4-dione Using Various Acid Catalysts 75 parts by weight of a 50% strength aqueous glyoxylic acid (0.5 mol glyoxylic acid) and the catalyst are placed in a heatable, stirred apparatus. The mixture is subsequently heated to an internal temperature of 100° C. while stirring. 75 parts by weight of benzylurea (corresponds to 0.5 mol) are then added at a constant rate over a period of 30 minutes. After addition of the benzylurea is complete, the reaction mixture is stirred at 100° C. for another 30 minutes, a sample is taken and analysed by HPLC. Table 1 shows the composition of the organic components of the reaction mixtures examined. The following reaction equation shows the formulae of the compounds which can be formed.

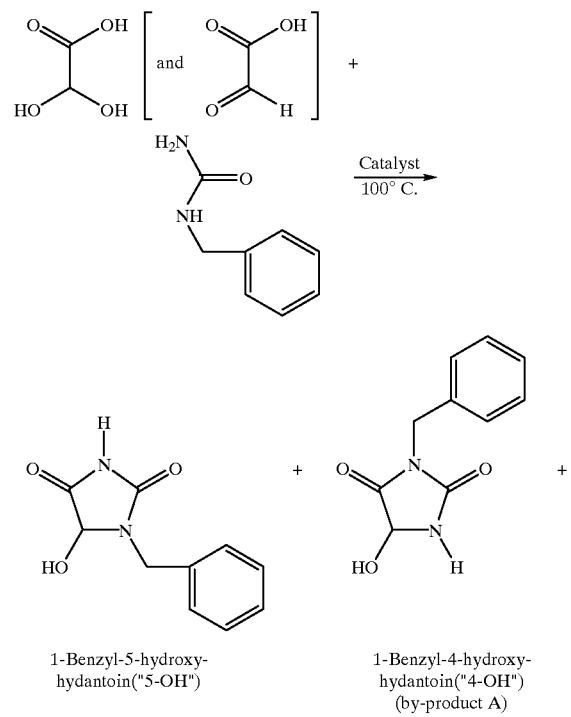

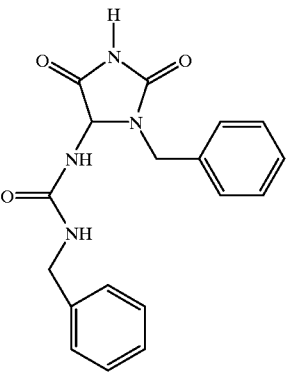

5-Benzylurea-1-benzyl-
hydantoin
(by-product B)

TABLE 1

(all quantities in parts reported in the table are parts by weight)

| Catalyst | Benzyl-urea % by weight | "5-OH" % by weight | By-product "A" % by weight | By-product "B" % by weight |
|---|---|---|---|---|
| 75 parts of acetic acid | 1.0 | 76.2 | 15.8 | 7.0 |
| 75 parts of formic acid | 0.7 | 67.5 | 14.7 | 17.1 |
| 10 parts of boric acid dissolved in 75 parts of $H_2O$ | 0.3 | 78.7 | 9.7 | 11.4 |
| 10 parts of phosphoric acid dissolved in 75 parts of $H_2O$ | 0.8 | 66.7 | 17.6 | 14.9 |
| 10 parts of oxalic acid dissolved in 75 parts of $H_2O$ | 1.8 | 63.9 | 21.9 | 12.5 |
| 10 parts of $Na_2HPO_4$ dissolved in 75 parts of $H_2O$ | 7.0 | 69.0 | 9.1 | 14.9 |
| 10 parts of $KH_2PO_4$ dissolved in 75 parts of $H_2O$ | 3.6 | 73.7 | 10.7 | 12.0 |
| 10 parts of $KHSO_4$ dissolved in 75 parts of $H_2O$ | 1.4 | 65.6 | 20.2 | 12.9 |
| 10 parts of $CH_3COONa$ dissolved in 75 parts of $H_2O$ | 16.4 | 65.7 | 3.3 | 14.6 |

EXAMPLE 2

Preparation of 1-benzyl-5-hydroxy-imidazoline2,4-dione 3000 parts by weight of 50% strength aqueous glyoxylic acid solution and 500 parts by weight of acetic acid (100% strength) are placed in a heatable, stirred apparatus and heated to 100° C. A mixture of 3000 parts by weight of benzylurea, 1300 parts by weight of water and 1500 parts by weight of acetic acid having a temperature of 80° C. is added to this solution over a period of one hour. The total reaction mixture is subsequently stirred at an internal temperature of 100° C. for another hour. 4500 parts by weight of an acetic acid/water mixture are then distilled off to a pressure of 200 mbar and a temperature at the bottom of 100° C. The remaining liquid residue is admixed at 90° C. with 900 parts by weight of water and 12.5 parts by weight of acetic acid, cooled to 35° C., admixed with 3000 parts by weight of methylene chloride and stirred at 25° C. for 12 hours. The temperature is then held at 3° C. for 1 hour by cooling.

The resulting crystal slurry is filtered, the crystals are washed with 1500 parts by weight of water and 2500 parts by weight of methylene chloride and dried to constant weight by drawing nitrogen through them.

This gives 2281 parts by weight of a white solid having the following composition:

|  | % by weight |
|---|---|
| Benzylurea | 0 |
| "5-OH" | 97.2 |
| By-product A | 2.8 |
| By-product B | 0 |
| Water | 0.05 |

EXAMPLE 3

Preparation of 1-benzyl-5-ethoxy-imidazoline-2,4-dione using Triethyl Orthoformate without Intermediate Isolation of the 1-benzyl-5-hydroxy-imidazoline-2,4-dione 3000 parts by weight of 50% strength aqueous glyoxylic acid solution and 500 parts by weight of acetic acid are placed in a heated, stirred apparatus and heated to an internal temperature of 100° C. while stirring. A mixture of 3000 parts by weight of benzylurea and 2000 parts by weight of acetic acid having a temperature of 80° C. is added to this solution over a period of 1 hour. The reaction mixture is then stirred at 100° C. for 2 hours. After this time, 4000 parts by weight of an acetic acid/water mixture are distilled off at a temperature of 100–110° C. over a period of 2 hours to a pressure of 300 mbar. The residue from this distillation is admixed at 80° C. with 2000 parts by weight of toluene and distilled at a temperature at the bottom of 100° C. and a pressure of 300 mbar. 1000 parts by weight of ethanol, 3000 parts by weight of triethyl orthorformate and 50 parts by weight of $H_2SO_4$ are then added to the residue and the mixture is heated at 80° C. for one hour. During this time, 100 parts by weight of solvent mixture, predominantly ethyl formate, are distilled off. Subsequently, a mixture of 3000 parts by weight of ethyl acetate and 6000 parts by weight of n-hexane is added to the residue and the resulting solution is then stirred for 8 hours at 25° C. and 3 hours at 3° C. The crystalline precipitate formed is filtered off and dried to constant weight.

This gives 2000 parts by weight of 94% pure 1-benzyl-5-ethoxy-imidazoline-2,4-dione.

EXAMPLE 4

Preparation of 1-benzyl-5-ethoxy-imidazoline-2,4-dione from isolated 1-benzyl-5-hydroxy-imidazoline-2,4-dione using Thionyl Chloride and Ethanol 309 parts by weight of 1-benzyl-5-hydroxy-imidazoline-2,4-dione from Example 2 and 375 parts by weight of toluene are placed in a heatable, stirred apparatus which is connected to a gas scrubber. The reaction mixture is firstly heated to boiling for a brief period in order to remove remaining traces of water. The reaction mixture is then cooled to 90° C. and 196.5 parts by weight of thionyl chloride are added at this temperature while stirring over a period of 4 hours. A constant, strong stream of gas (HCl and $SO_2$) is evolved from the reaction vessel. After 4 hours, the reaction mixture has become a light-coloured, yellowish solution and gas evolution has ceased. The toluene is subsequently distilled off at a temperature of 90° C. and a pressure of 200 mbar. The internal temperature in the reaction vessel is then reduced to 80° C., and 450 parts by weight of ethanol are added over a period of 3 hours. The mixture is subsequently stirred for another 2 hours at a temperature of 82° C. 7 parts by weight of activated carbon are then added to the clear, light-coloured reaction solution and the mixture is stirred for 15 minutes. The activated carbon is subsequently separated off by means of a clarifying filter and the filtrate is cooled to 3° C. while stirring. The resulting crystal slurry is filtered and the crystalline product is dried to constant weight.

This gives 278.3 parts by weight of product which, according to analysis, contains 98.2% of 1-benzyl-5-ethoxy-imidazoline-2,4-dione and 1.8% of ethanol.

EXAMPLES 5(1)–5(7)

Preparation of further 1-substituted 5-hydroxy-imidazoline-2,4-diones

Further 1-substituted 5-hydroxy-imidazoline-2,4-diones are prepared in an identical manner to Example 2 by reacting the amounts specified below of the N-substituted urea in an apparatus as described in Example 2, and these products have the following properties:

EXAMPLE 5(1)

5-Hydroxy-1-(3-phenylpropyl)-imidazoline-2,4-dione, $C_{12}H_{14}N_2O_3$ is prepared using 3560 parts by weight of 3-phenylpropylurea.

Mp.: 131–132° C., MS: molecular peak 234, NMR (400 MHz; DMSO $D_6$): 1.7–1.9 (m, 2H); 2.6 (t, 2H); 3.25 (m, 2H); 5.1 (d, I=11 Hz, 1H); 6.85 (d, I=11 Hz, 1H, replaceable by D); 7.15–7.30 (m, 5H); 10.75 (s, 1H, replaceable by D)

EXAMPLE 5(2)

5-Hydroxy-1-(3,4-dimethoxybenzyl)-imidazoline-2,4-dione, $C_{12}H_{14}N_2O_5$ is prepared using 4260 parts by weight of n-veratrylurea.

Mp.: 143–144° C., MS: molecular peak 266, NMR (400 MHz; DMSO $D_6$): 3.75 (s, 6H); 4.3 (dd, $I_1$=83 Hz, $I_2$=17 Hz, 2H); 4.95 (d, I=10 Hz, 1H); 6.85–6.95 (m, 3H); 7.0 (d, I=10 Hz, 1H, replaceable by D); 10.85 (s, 1H, replaceable by D)

EXAMPLE 5(3)

5-Hydroxy-1-(1-phenylethyl)-imidazoline-2,4-dione, $C_{11}H_{12}N_2O_3$ is prepared using 3330 parts by weight of DL-1-phenylethylurea.

Mp.: 139–140° C., MS: molecular peak 220, NMR (400 MHz; DMSO $D_6$): 1.55–1.65 (t, 3H); 4.85 (d, I=9 Hz, 1H); 5.0–5.1 (q, 1H); 6.9 (d, I=9 Hz, 1H, replaceable by D); 7.25–7.45 (m, 5H); 10.8 (s, 1H, replaceable by D)

EXAMPLE 5(4)

5-Hydroxy-1-(4-methylbenzyl)-imidazoline-2,4-dione, $C_{11}H_{12}N_2O_3$ is prepared using 3030 parts by weight of 4-methylbenzylurea.

Mp.: 174° C., MS: molecular peak 220, NMR (400 MHz; DMSO $D_6$): 2.3 (s, 3H); 4.35 (dd, $I_1$=90 Hz, $I_2$=12 Hz, 2H); 4.9 (d, I=9 Hz, 1H); 7.0 (d, I=9 Hz, 1H, replaceable by D); 7.1–7.2 (m, 4H); 10.9 (s, 1H, replaceable by D)

EXAMPLE 5(5)

5-Hydroxy-1-(4-chlorobenzyl)imidazoline-2,4-dione, $C_{10}H_9ClN_2O_3$ is prepared using 3120 parts by weight of 4-chlorobenzylurea.

Mp.: 149–150° C., MS: molecular peak 240, NMR (400 MHz; DMSO $D_6$): 4.4 (dd, I=55 Hz, $I_2$=15 Hz, 2H); 5.0 (d, I=10 Hz, 1H); 7.0 (d, I=10 Hz, 1H, replaceable by D); 7.3–7.4 (m, 4H); 10.9 (s, 1H, replaceable by D)

EXAMPLE 5(6)

5-Hydroxy-1-[2-(4-chlorophenyl)ethyl]-imidazoline-2,4-dione, $C_{11}H_{11}ClN_2O_3$ is prepared using 3350 parts by weight of 4-chloroethylphenylurea.

Mp.: 151–152° C., MS: molecular peak 254, NMR (400 MHz; DMSO $D_6$): 2.75–2.9 (m, 2H); 3.3–3.6 (m, 2H); 5.05 (d, I=11 Hz, 1H); 6.95 (d, I=11 Hz, 1H, replaceable by D); 7.25–7.40 (m, 4H); 10.75 (s, 1H, replaceable by D)

EXAMPLE 5(7)

5-Hydroxy-1-(2-Phenylethyl)imidazoline-2,4-dione, $C_{11}H_{12}N_2O_3$ is prepared using 3320 parts by weight of 2-phenylethylurea.

Mp.: 168–169° C., MS: molecular peak 220, NMR (400 MHz; DMSO $D_6$): 2.75–2.9 (m, 2H); 3.3–3.6 (m, 2H); 5.0 (d, I=10 Hz, 1H); 6.95 (d, I=10 Hz, 1H, replaceable by D); 7.2–7.35 (m, 5H); 10.8 (s, 1H, replaceable by D)

EXAMPLES 6(1)–6(7)

Preparation of Various 1-benzyl-5-alkoxy-imidazoline-2,4-diones Starting from Isolated 1-benzyl-5-hydroxy-imidazoline-2,4-dione using Thionyl Chloride and the Corresponding Alcohols In an apparatus as described in Example 4, the following further 1-benzyl-5-alkoxy-imidazoline-2,4-diones are prepared under the same reaction conditions from 309 parts by weight of 1-benzyl-5-hydroxy-imidazoline-2,4-dione from Example 2 and the corresponding alcohols:

EXAMPLE 6(1)

1-Benzyl-5-methoxy-imidazoline-2,4-dione, $C_{11}H_{12}N_2O_3$.

Mp.: 116° C., MS: molecular peak 220, NMR (400 MHz, DMSO $D_6$): 3.1 (s, 3H); 4.4 (dd, $I_1$=44 Hz, $I_2$=11 Hz, 2H); 5.05 (s, 1H); 7.25–7.40 (m, 5H); 11.15 (s, 1H, replaceable by D)

EXAMPLE 6(2)

1-Benzyl-5-propoxy-imidazoline-2,4-dione, $C_{13}H_{16}N_2O_3$.

Mp.: 72° C., MS: molecular peak 248, NMR (400 MHz, DMSO $D_6$): 0.7–0.8 (t, 3H); 1.25–145 (m, 2H); 3.15–3.35 (m, 2H); 4.45 (dd, $I_1$=36 Hz, $I_2$=12 Hz, 2H); 5.1 (s, 1H); 7.25–7.40 (m, 5H); 11.15 (s, 1H, replaceable by D)

EXAMPLE 6(3)

1-Benzyl-5-isopropoxy-imidazoline-2,4-dione, $C_{13}H_{16}N_2O_3$.

Mp.: 61° C., MS: molecular peak 248, NMR (400 MHz, DMSO $D_6$): 0.95–1.0 (d, 3H); 1.05–1.1 (d, 3H); 3.75–3.85 (m, 1H); 4.45 (dd, $I_1$=67 Hz, $I_2$=17 Hz, 2H); 5.0 (s, 1H); 7.25–7.40 (m, 5H); 11.03 (s, 1H, replaceable by D)

EXAMPLE 6(4)

1-Benzyl-5-butoxy-imidazoline-2,4-dione, $C_{14}H_{18}N_2O_3$.

Mp.: 76° C., MS: molecular peak 262, NMR (400 MHz, DMSO $D_6$): 0.75–0.85 (t, 3H);1.1–1.4 (m, 4H); 3.2–3.4 (m, 2H); 4.4 (dd, $I_1$=34 Hz, $I_2$=17 Hz, 2H); 5.1 (s, 1H); 7.24–7.40 (m, 5H); 11.15 (s, 1H, replaceable by D)

EXAMPLE 6(5)

1-Benzyl-5-isobutoxy-imidazoline-2,4-dione, $C_{14}H_{18}N_2O_3$.

Mp.: 87° C., MS: molecular peak 262, NMR (400 MHz, DMSO $D_6$): 0.7–0.8 (t, 6H); 1.55–1.65 (m, 1H); 3.0–3.2 (m, 2H); 4.45 (dd, $I_1$=39 Hz, $I_2$=17 Hz, 2H); 5.1 (s, 1H); 7.25–7.40 (m, 5H); 11.1 (s, 1H, replaceable by D)

EXAMPLE 6(6)

1-Benzyl-5-octyloxy-imidazoline-2,4-dione, $C_{18}H_{26}N_2O_3$.

Mp.: 53° C., MS: molecular peak 318, NMR (400 MHz, DMSO $D_6$): 0.8–0.9 (t, 3H); 1.1–1.35 (m, 12H); 3.2–3.4 (m, 2H); 4.45 (dd, $I_1$=28 Hz, $I_2$=17 Hz, 2H); 5.05 (s, 1H); 7.25–7.35 (m, 5H); 11.15 (s, 1H, replaceable by D)

EXAMPLE 6(7)

1-Benzyl-5-[(2-ethylhexyl)oxy]-imidazoline-2,4-dione, $C_{18}H_{26}N_2O_3$.

Mp.: 67–68° C., MS: molecular peak 302, NMR (400 MHz, DMSO $D_6$): 0.7–0.85 (m, 6H); 1.1–1.25 (m, 9H); 3.1–3.25 (m, 2H); 4.45 (dd, $I_1$=39 Hz, $I_2$=17 Hz, 2H); 5.1 (s, 1H); 7.25–7.40 (m, 5H); 11.15 (s, 1H, replaceable by D)

EXAMPLE 7

Preparation of 5-ethoxy-1-(3-phenylpropyl)-imidazoline-2,4-dione

Using a method analogous to EXAMPLE 4, 5-ethoxy-1-(3-phenylpropyl)-imidazoline-2,4-dione is prepared by reacting 5-hydroxy-1-(3-phenylpropyl)-imidazoline-2,4-dione from EXAMPLE 5(1) with thionyl chloride and ethanol. The substance $C_{14}H_{18}N_2O_3$ has a melting point mp.: 64° C. MS: molecular peak 262, NMR (400 MHz, DMSO $D_6$): 1.1–1.15 (t, 3H); 1.75–1.9 (m, 2H); 2.55–2.65 (t, 2H); 3.1–3.6 (m, 4H); 5.15 (s, 1H); 7.15–7.3 (m, 5H); 11.0 (s, 1H, replaceable by D)

EXAMPLE 8

Preparation of 5-ethoxy-1-(2-phenylethyl)-imidazoline-2,4-dione

Using a method analogous to EXAMPLE 4, 5-ethoxy-1-(2-phenylethyl)-imidazoline-2,4-dione is prepared by reacting 5-hydroxy-1-(2-phenylethyl)-imidazoline-2,4-dione from EXAMPLE 5(7) with thionyl chloride and ethanol.

The substance $C_{13}H_{16}N_2O_3$ has a melting point mp. of 120° C. MS: molecular peak 248, NMR (400 MHz, DMSO $D_6$): 1.1–1.15 (t, 3H); 1.75–1.9 (m, 2H); 2.55–2.65 (t, 2H); 3.1–3.6 (m, 2H); 5.15 (s, 1H); 7.15–7.3 (m, 5H); 11.0 (s, 1H, exchangeable with D).

COMPARATIVE EXAMPLE 9

Reaction of N-alkylureas with Glyoxylic Acid

In an apparatus as described in EXAMPLE 2, attempts are made to prepare 1-alkyl-5-hydroxy-imidazoline-2,4-diones by reaction of the corresponding N-alkylureas under the conditions described in EXAMPLE 2.

74 parts by weight of N-methylurea are introduced in a number of small, equal portions into 148 parts by weight of 50% strength glyoxylic acid, 100 parts by weight of water and 100 parts by weight of acetic acid at 100° C. over a period of 1 hour. The reaction mixture is stirred for another 1 hour at 100° C. and subsequently worked up as described in EXAMPLE 2. This gives only 37 parts by weight of a greasy crystalline product which cannot be purified by crystallization from customary solvents (ethanol, diethyl ether, methylene chloride, toluene, ethyl acetate). NMR analysis of the crystalline product indicates many substances including the two isomeric hydantoins: 1-methyl-5-hydroxy-imidazoline-2,4-dione with the characteristic NH signal at 11.1 ppm and the isomeric 3-methyl-5-hydroxy-imidazoline-2,4-dione with the characteristic NMR signal at 8.6 ppm. The yield of both hydantoins is estimated at not more than 10% in each case from the NMR spectrum.

The reactions of N-butylurea, N-octylurea and N-dodecylurea with glyoxylic acid give similarly sticky products from which no uniform products can be isolated and whose NMR spectra indicate many other substances in addition to the desired 1-alkyl-5-hydroxyimidazoline-2,4-diones.

Although the present invention has been described in detail with reference to certain preferred versions thereof, other variations are possible. Therefore, the spirit and scope appended claims should not be limited to the description of the versions contained therein.

What is claimed is:

1. Process for preparing 1-substituted 5-hydroxy-imidazoline-2,4-diones of the formula (I)

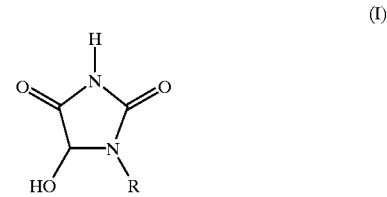

wherein R represents a substituted or unsubstituted $C_6$–$C_{12}$-aryl radical or a substituted or unsubstituted $C_7$–$C_{18}$-aralkyl radical, comprising reacting glyoxylic acid with an N-substituted urea of the formula RNH—CO—$NH_2$, wherein R is as defined above, in an aqueous solution having a strength ranging from about 10 to about 80% in the presence of an acid catalyst.

2. Process according to claim 1, wherein the N-substituted ureas have an R that represents a substituted or unsubstituted $C_6$–$C_{10}$-aryl radical or a substituted or unsubstituted $C_7$–$C_{12}$-aralkyl radical.

3. Process according to claim 1, wherein R represents a benzyl radical.

4. Process according to claim 1, wherein the aryl radicals in the radical R are substituted by 1, 2, 3, 4 or 5 identical or different radicals selected from the group consisting of halogen, $C_1$–$C_{12}$-alkyl, $NO_2$ and $C_1$–$C_{12}$-alkoxy.

5. Process according to claim 1, wherein the acid catalyst is a protic acid.

6. Process according to claim 5, wherein the acid catalyst is formic acid, acetic acid, propionic acid, oxalic acid, boric acid, potassium or sodium dihydrogenphosphate, potassium or sodium hydrogen-phosphate, phosphoric acid, or alkali metal hydrogensulphates.

7. Process according to claim 1, wherein the molar ratio of glyoxylic acid to the N-substituted urea is (0.5–5).

8. The process of claim 4, wherein the halogen radicals that substitute the radical R are chlorine radicals, the $C_1$–$C_{12}$-alkyl radicals are methyl radicals, and the $C_1$–$C_{12}$-alkoxy radicals are selected from the group consisting of methoxy and phenoxy radicals.

9. The process of claim 7, wherein the molar ratio of glyoxylic acid to the N-substituted urea is from about 0.8:1 to about 2:1.

10. A process for preparing a 1-substituted 5-hydroxy-imidazoline-2,4-dione of the formula (I)

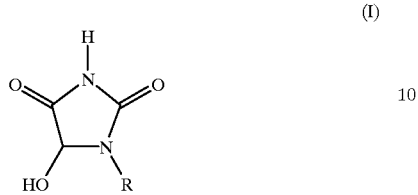

(I)

wherein R represents a substituted or unsubstituted $C_6$–$C_{12}$-aryl radical or a substituted or unsubstituted $C_7$–$C_{18}$-aralkyl radical, comprising reacting glyoxylic acid with an N-substituted urea of the formula RNH—CO—NH$_2$, wherein R is as defined above, in an aqueous solution having a strength ranging from about 10 to about 80% in the presence of an acid catalyst, wherein 1-substituted 5-hydroxy-imidazoline-2,4-dione is isolated by crystallization.

11. The process of claim 10, wherein the 1-substituted 5-hydroxy-imidazoline-2,4-dione is isolated by crystallization in the presence of an organic solvent.

12. The process of claim 11, wherein the organic solvent is selected from the group consisting of methylene chloride, chlorobenzene, aliphatic alcohols, and esters.

13. The process of claim 10 further comprising a 1-substituted 5-hydroxy-imidazoline-2,4-dione of the formula I reacting In a further step and thereby converting to a 1-substituted 5-alkoxy-imidazoline-2,4dione of the formula (II)

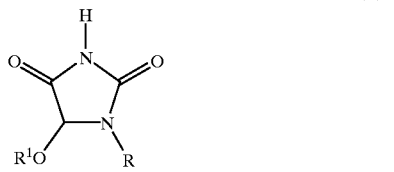

(II)

wherein R represents a substituted or unsubstituted $C_8$–$C_{12}$-aryl radical or a substituted or unsubstituted $C_7$–$C_{18}$-aralkyl radical, and $R^1$ represents a straight-chain or branched $C_1$–$C_{18}$-alkyl radical, wherein the 1-substituted 5-hydroxy-imidazoline-2,4-dione of the formula (I) converts into the 1-substituted 5-alkoxy-imidazoline-2,4-dione of the formula (II) by one of the following reactions:
(1) the 1-substituted 5-hydroxy-imidazoline-2,4-dione of the formula (I) reacts in the presence of an acid catalyst, with an alcohol of the formula $R^1OH$, wherein $R^1$ represents a straight-chain or branched $C_1$–$C_{18}$-alkyl radical,
(2) the 1-substituted 5-hydroxy-imidazoline-2,4-dione of the formula I reacts with a tri-$C_1$–$C_{18}$-alkyl orthoformate, or
(3) the 1-substituted 5-hydroxy-imidazoline-2,4-dione of the formula (I) reacts with a thionylchloride and subsequently reacts with an alcohol of the formula $R^1OH$, wherein $R^1$ represents a straight-chain or branched $C_1$–$C_{18}$-alkyl radical.

14. The process of claim 13, wherein the 1-substituted 5-hydroxy-imidazoline-2,4-dione of the formula I reacts with an alcohol of the formula $R^1OH$ in the presence of an acid catalyst to form the 1-substituted 5-alkoxy-imidazoline-2,4-dione of the formula II.

15. The process of claim 13, wherein the 1-substituted 5-hydroxy-imidazoline-2,4-dione of the formula I reacts with tri-($C_1$–$C_{18}$)-alkyl orthoformate to form the 1-substituted 5-alkoxy-imidazoline-2,4-dione of the formula II.

16. The process of claim 13, wherein the 1-substituted 5-hydroxy-imidazoline-2,4-dione of the formula I reacts firstly with thionyl chloride and subsequently with an alcohol $R^1OH$, where $R^1$ is as defined above, to form the 1-substituted 5-alkoxy-imidazoline-2,4-dione of the formula II.

17. At The process of claim 16, wherein the straight-chain or branched $C_1$–$C_{18}$-alkyl radical is selected from the group consisting of methyl, ethyl, propyl, iso-propyl, butyl, iso-butyl, octyl and 2-ethylhexyl.

* * * * *